United States Patent [19]
Vancaillie

[11] Patent Number: 5,395,354
[45] Date of Patent: Mar. 7, 1995

[54] VAGINAL SPECULUM AND FLUID COLLECTOR FOR ENDOSCOPIC SURGERY

[76] Inventor: Thierry G. Vancaillie, 133 Pin Oak Forest, San Antonio, Tex. 78232

[21] Appl. No.: 109,121

[22] Filed: Aug. 19, 1993

[51] Int. Cl.$^6$ .............................................. A61M 1/00
[52] U.S. Cl. .................................... 604/317; 604/327; 604/328; 604/329; 604/330; 128/3; 128/846; 128/849; 128/853
[58] Field of Search ................... 128/3, 12, 14, 17, 19, 128/20, 846, 849, 851, 853, 856, 887; 604/317, 322, 324, 327–330

[56] References Cited

U.S. PATENT DOCUMENTS

| | | | |
|---|---|---|---|
| 3,452,750 | 7/1969 | Blanford | 128/853 |
| 3,528,423 | 9/1970 | Lee | 604/329 |
| 4,010,740 | 3/1977 | Littorin | 128/17 |
| 4,105,019 | 8/1978 | Haswell | 128/849 |
| 4,632,093 | 12/1986 | Giorni | 128/12 |
| 5,115,799 | 5/1992 | McGann | 128/12 |
| 5,322,071 | 6/1994 | Ambrose | 128/849 |

Primary Examiner—Randall L. Green
Assistant Examiner—P. Zuttarelli
Attorney, Agent, or Firm—Gambrell, Wilson & Hamilton

[57] ABSTRACT

A malleable vaginal speculum is manually shaped to dilate the inner contour of a vagina sufficiently to allow manipulation of endoscopic surgical instruments within the vagina. The malleable vaginal speculum may optionally be coupled a funnel, apron and splash shield to function as a fluid collector for use during endoscopic surgery. A portion of the splash shield is placed under the patient while the remainder extends to a perforated portion of the funnel wall. Fluid draining into the funnel through its mouth and through the perforated wall is collected in a container, where its volume is measured. By measuring the volume of irrigation fluid dispensed during the surgery and subtracting the measured fluid volume collected, an estimate of the amount of irrigation fluid absorbed by the patient during the surgery is obtained.

3 Claims, 6 Drawing Sheets

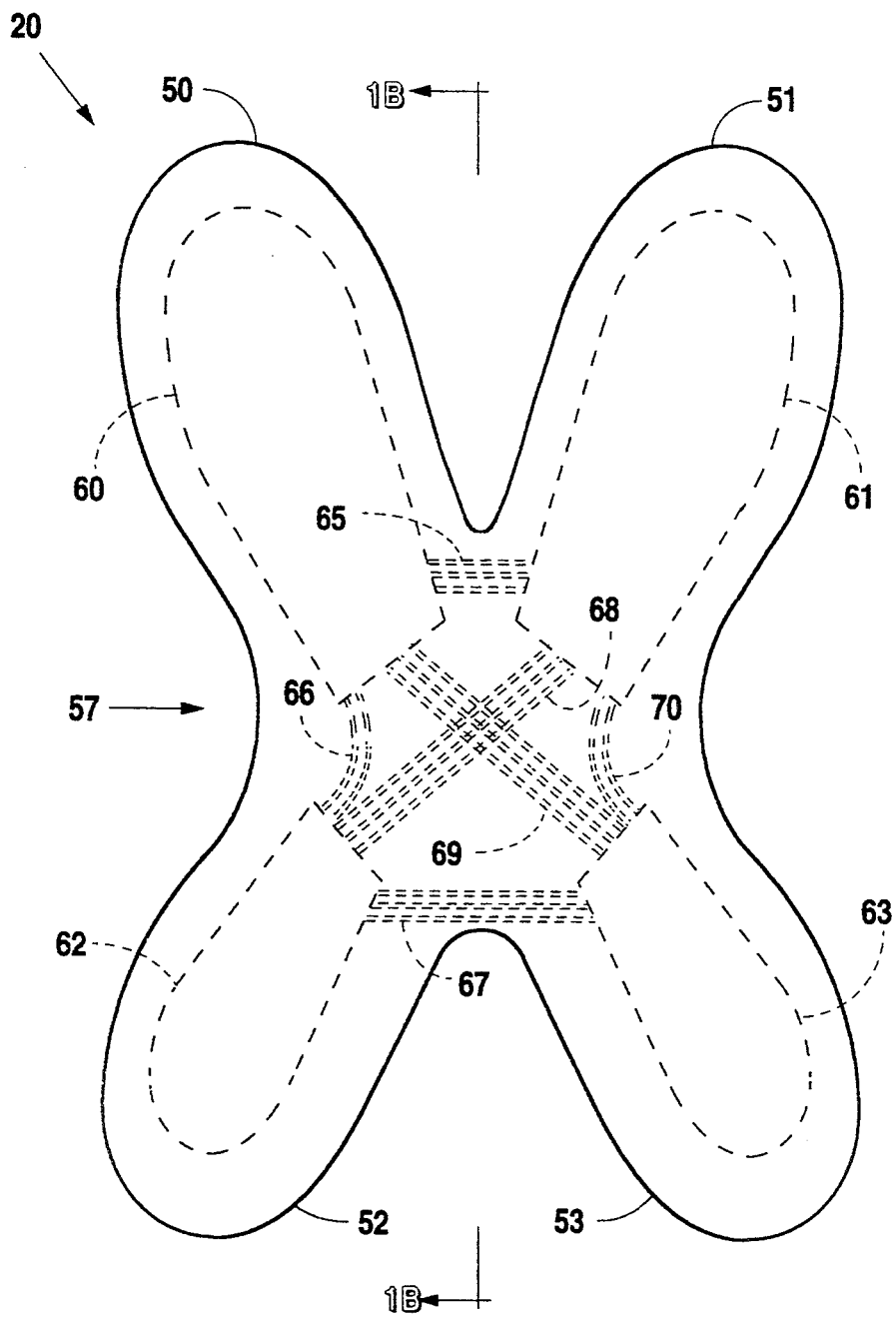
Fig. 1A
Fig. 1B

VAGINAL SPECULUM AND FLUID COLLECTOR FOR ENDOSCOPIC SURGERY

BACKGROUND

1. Field of the Invention

The invention relates to methods and apparatus to facilitate transvaginal endoscopic surgery.

2. Endoscopic Uterine Surgery

Endoscopic surgery is frequently performed on the uterus transvaginally. This anatomic approach requires sufficient dilation of the vaginal canal to allow manipulation of the surgical instruments and to give the surgeon enough visibility to properly guide the endoscope. In an anesthetized patient, a weighted speculum is commonly employed to maintain the desired degree of vaginal dilation, but the speculum occasionally interferes with free movement of the endoscope. Another disadvantage of a weighted speculum is that its presence impedes the collection and accurate measurement of fluid drainage from the vagina.

Fluid drains continuously from the vagina during transvaginal endoscopic surgery because a continuous flow of water-based irrigation fluid passes through the endoscope from an external reservoir. Irrigation fluid flow in the area of surgery removes small pieces of excised tissue and blood, continually clearing the surgeoffs endoscopic view of the operative site(s). Most of the irrigation fluid which enters the uterus through the endoscope is subsequently flushed out through the cervix and vagina by additional irrigation fluid. However, a portion of the entering fluid is absorbed through the endometrium and through parts of the patient's vascular system exposed by the surgery. During relatively prolonged and/or invasive uterine surgery, sufficient fluid may be absorbed to substantially adversely alter the patient's serum electrolyte balance. Because serious electrolyte imbalances may result in seizures, coma or death of the patient, the surgeon must have sufficient warning of impending imbalances to take corrective action. Hence, frequent estimates of serum electrolyte levels may be required during certain endoscopic uterine surgical procedures.

Serum electrolytes are conventionally determined by laboratory analysis of blood samples obtained by venipuncture. Repeated sampling in this manner, however, is disturbing to the patient and unnecessary. A more convenient method for estimating serum electrolyte levels relies on accurate determination of baseline electrolyte concentrations, combined with estimates of the amount of absorbed irrigation fluid.

Estimates of absorbed irrigation fluid, however, are presently relatively inaccurate because of difficulty in monitoring the total amount of fluid which drains from the vagina, as well as that released through use of endoscopic instruments near the vagina. A fraction of the drained and released waste irrigation fluid typically falls on surgical drapes and thence to the operating table or floor, where it is commonly lost without being measured. Because the volume of this lost fraction of waste fluid is generally unknown, the amount of irrigation fluid absorbed by the patient is difficult to estimate accurately during the course of an operation.

SUMMARY OF THE INVENTION

The present invention relates to methods and apparatus for dilating the vaginal canal and for collecting and measuring waste irrigation fluid drained from the vagina and otherwise released through use of endoscopic instruments during transvaginal endoscopic surgery. Accurate measurement of waste irrigation fluid volume allows estimation of the amount of irrigation fluid absorbed by a patient.

Vaginal dilation is generally preferred for any transvaginal surgical procedure, regardless of its duration or complexity, because the surgeon must have clearance to safely insert and manipulate the surgical instruments. On the other hand, collection and measurement of waste irrigation fluid may be safely omitted for relatively short and/or minimally invasive procedures. Hence, methods and apparatus of the present invention for dilating the vaginal canal may preferably be used alone or in conjunction with methods and apparatus for collecting and measuring waste irrigation fluid.

Methods of vaginal dilation according to the present invention relate to use of a malleable speculum which can be manually shaped to dilate the vagina and, in some embodiments, manually trimmed to fit a particular patient. When the planned duration and/or invasiveness of the surgical procedure require estimation of serum electrolyte levels, the present invention also comprises methods for estimating absorbed fluid which complement use of a malleable speculum. Such a method of estimating an amount of irrigation fluid absorbed by a patient undergoing endoscopic surgery comprises dispensing a measured amount of irrigation fluid during the surgery, directing waste irrigation fluid into a funnel via an apron, directing waste irrigation fluid into said funnel via a splash shield (and, in certain embodiments, a one-way valve), collecting a measured amount of waste irrigation fluid directed into said funnel, subtracting said measured amount of fluid collected from said measured amount of irrigation fluid dispensed during the surgery to form a fluid difference amount, and estimating said fluid difference amount as an amount of irrigation fluid absorbed by the patient undergoing endoscopic surgery.

The amount of fluid collected through use of this method ideally comprises substantially the entire volume of waste irrigating fluid drained from the vagina or released from the endoscope near the vagina, including that which would frequently be difficult to accurately estimate (e.g., that portion which is splashed or drains on the operating table and surgical drapes).

The present invention includes a malleable speculum, which may be used independently or may be sealingly coupled either reversibly or substantially irreversibly to an apron-funnel-splash shield assembly to facilitate collection of waste fluid drainage. The malleable speculum may be used without the apron-funnel-splash shield assembly for operations wherein accurate estimation of the amounts of drained and absorbed irrigation fluid is regarded as unnecessary because the absorption of clinically significant amounts is unlikely. However, because the duration and/or invasive character of a surgical procedure may be difficult to precisely predict, a requirement for collection and accurate measurement of drainage fluid may often be presumed. Thus, the malleable speculum may often be present in a preferred embodiment of the present invention as part of an assembly comprising a speculum, an apron, a funnel, and a splash shield. This assembly acts to provide the desired degree of vaginal dilation and to improve the accuracy of fluid absorption estimates during endoscopic surgery. The latter function includes collecting and measuring both the irrigation fluid which falls directly on components of the fluid collector and that which reaches the collector after flowing over the patient or portions of the surgical and operating room support apparatus associated with the operation.

The speculum-apron-funnel-splash shield assembly as a whole functions as a fluid collector. In detail, this fluid collector comprises a malleable speculum which has a longitudinal axis and a coupling area. In clinical use, the speculum is manually molded to establish and maintain the inner contour of a vagina which is sufficiently dilated to allow the Use of surgical instruments within the vagina. During a surgical procedure, the malleable speculum efficiently directs irrigation fluid which drains over its superior surface from the vagina into the funnel via a flexible (preferably substantially trapezoidal) membrane called the apron. The apron has a first apron edge spaced substantially apart from a second apron edge, said first apron edge being sealingly coupled to the malleable speculum proximate said coupling area.

The apron is also coupled to a funnel. The funnel, having a funnel mouth and a perforated wall section, is sealingly coupled to the second apron edge proximate the funnel mouth so that fluid flowing over the superior surface of the apron will be directed into the funnel mouth. The apron may be shaped with malleable stays to have a concave-upward configuration effective for directing the flow of waste fluid flowing over it toward the funnel mouth. Additionally, the funnel mouth may preferably be held open with manually-adjustable malleable stays coupled to the funnel mouth. It is thus adapted to receive waste fluid which may fall directly into it from above, as from an endoscope being examined by the surgeon prior to insertion in the vagina.

The funnel may also receive waste fluid which does not pass through the funnel mouth (i.e., a first funnel fluid entrance) but passes instead through the perforated wall section (i.e., a second funnel fluid entrance). Waste fluid thus directed to flow into the funnel through the perforations has previously been carried to the funnel by a splash shield which is sealingly coupled to the outer surface of the funnel wall. The splash shield has a first splash shield edge spaced substantially apart from a second splash shield edge, the first splash shield edge being sealingly coupled to the funnel proximate the perforated wall section so as to direct fluid flowing over the superior surface of the splash shield to continue flowing through the funnel wall perforations (i.e., the coupling is substantially inferior to the perforations when the funnel is positioned for use). The splash shield may incorporate malleable stays to maintain a concave-upward configuration where necessary to prevent flow of waste fluid from the superior surface of the splash shield except through the funnel wall perforations.

The splash shield second edge is intended for placement in use under the patient's buttocks. The splash shield which would then lie between the first and second edges (i.e., between the buttocks and funnel portion) acts in use to collect and direct the flow of irrigation fluid which may leak or drain around the malleable speculum and/or apron portions, or which might otherwise be substantially deposited on the operating table or surgical drapes. This fluid eventually flows by gravity through the perforations in the wall of the funnel (i.e., the second fluid entrance to the funnel) and thence via the funnel into a measuring-collecting container.

Note that the perforations comprising the second fluid entrance are optionally but preferably substantially covered by a flexible waterproof or water resistant flow diverter sheet which is sealingly coupled along a superior portion of its periphery to the inner surface of the funnel proximate the perforated wall section. That is, the flow diverter sheet is sealingly coupled to the opposite side of the funnel from that to which the splash shield is sealingly coupled. In use, the flow diverter sheet acts to prevent fluid which flows over the superior surface of the apron and into the funnel mouth from then flowing through the funnel wall perforations and out of the funnel. The flow diverter sheet instead directs fluid flowing over the superior surface of the apron and into the funnel mouth so it remains inside the funnel for collection and measurement. While preventing fluid flow from inside the funnel to outside the funnel through the perforations, the flow diverter sheet simultaneously allows fluid flowing over the superior surface of the splash shield to enter the funnel through the perforations, acting in use as a one-way valve (i.e., a flap valve).

The apron, funnel, and splash shield portions of the present invention are preferably substantially constructed of relatively lightweight, flexible, disposable, waterproof material (analogous to one or more of the materials commonly used to manufacture water-resistant surgical drapes), and are intended for efficient sterilization and use with a single patient only. The speculum is also intended for single patient use, but it preferably comprises relatively thicker material (e.g., polyethylene or silicone rubber) having a more malleable construction than the funnel, apron or splash shield. The latter structures, however, may be reinforced or stiffened with malleable stays to allow them to be manually shaped for more efficient use and/or better fit with any particular patient.

The speculum itself is preferably sufficiently malleable so that it may be manually reshaped from a substantially planar configuration to a folded or rolled configuration prior to insertion in the vagina of a patient in the lithotomy position. After it is inserted into the vagina of an anesthetized patient, the malleable speculum's circumference is preferably manually expanded about the longitudinal vaginal axis. Manual expansion of the circumference is preferably continued until sufficient vaginal patency is established to facilitate endoscopic surgery. The malleable speculum then maintains vaginal patency throughout the endoscopic surgical procedure while supporting at least a portion of the weight of the apron, funnel and splash shield which may depend from the speculum in use.

To achieve the desired level of malleability in the speculum, it may be reinforced with elongated longitudinal, transverse, and diagonal malleable stiffeners or stays such as metallic wires or strips, or stays of analogous malleable material (e.g., plastics, viscous gells and/or putty-like materials). The speculum may also comprise one or more sheets of malleable material e.g., a malleable sheet comprising tin, aluminum or other malleable metal, or a thermoplastic material. Such sheets may be encased in protective membranes or coatings to preclude substantial tissue contact with portions which may cause adverse reactions in a patient.

In preferred embodiments, the speculum is substantially planar, less than about 7 mm thick, and substantially symetrical about a longitudinal axis. When the speculum is inserted into a patient's vagina, the longitudinal axis of the speculum is substantially parallel to the longitudinal vaginal axis. The width of the speculum is preferably less than or equal to the vaginal wall circumference about its longitudinal axis when the vagina has been sufficiently dilated to accommodate effective use of surgical instruments (e.g., forceps, endoscope, or resectoscope). The speculum is also preferably sufficiently malleable so that it may be manually shaped to the inner contour of the dilated vagina, substantially retaining the dilated vaginal contour until the contour is manually altered by the surgeon or until the speculum is removed from the vagina. Because of variations in required material stiffness which may occur among different patients, malleable specula according to the present invention may be produced with differing material stiffness, representing differing degrees of malleability.

When in its planar configuration (i.e., prior to manual shaping), the malleable speculum has a symmetrical peripheral shape which is preferably substantially rectangular, polygonal, oval, or circular or a combination thereof. In certain preferred embodiments, the malleable speculum may comprise trimmable malleable material, i.e., malleable material which may be trimmed to its final shape using e.g., bandage scissors, prior to vaginal insertion by a surgeon.

A malleable speculum may thus be precut to a desired planar shape or trimmed to shape just prior to use. Preferred embodiments may comprise substantially planar configurations with optional peripheral shapes embossed, printed, or otherwise indicated on the planar surface as guides to surgeons for trimming the speculum to a desired shape. In this way, for example, provision for various speculum sizes may be made on a single, substantially planar sheet of malleable material, the surgeon trimming the shape of the material to fit each patient as needed.

Other preferred embodiments of the malleable speculum, however, may incorporate precut shapes determined to be particularly advantageous in certain surgical applications. One such preferred shape comprises two substantially plane and malleable upper arms (protuberances) coupled at a malleable junction. The speculum is sufficiently flexible to allow the upper arms to be manually made substantially coplanar or substantially parallel by bending the speculum about a longitudinal axis passing through the malleable junction. For insertion of the speculum in the vagina of a patient in the lithotomy position, the two upper arms are made substantially parallel by bending the speculum about its longitudinal axis. After placement within the vagina, the upper arms may then be spread and/or manually shaped to the vaginal contour. With the speculum thus inserted into the vagina and shaped to the vaginal contour, the malleable junction between the malleable arms preferably lies neither wholly within nor wholly outside the vagina, but rather substantially proximate the vaginal entrance.

The malleable junction between the malleable upper arms is intended for coupling the upper arms to each other and for coupling both upper arms to the apron portion via a coupling area. The coupling area is part of the speculum and, when coupled to the apron, aids in keeping the apron sufficiently deployed to effectively intercept fluid draining from the vagina over the speculum, subsequently directing the fluid flow to the funnel mouth and thence into the funnel for collection and measurement. In preferred embodiments, the malleable junction is therefore contiguous with both the upper arms and the coupling area of the speculum.

In use, the coupling area of the speculum preferably lies outside of the vagina and proximate the vaginal entrance. Depending on the strength and stiffness of the material chosen for the speculum and apron, the coupling area may, for example, have a substantially solid geometric shape (e.g., triangular or trapezoidal), or the malleable speculum as a whole (including the coupling area) may comprise a substantially planar cruciate (i.e., X-shaped) form comprising two malleable upper arms and two malleable lower arms, with a malleable junction coupling the upper arms with the lower arms. In the latter case, the coupling area comprises the two malleable lower arms (protuberances) of the X, a form similar to an inverted V in which the lower arms are intended to be coupled to the apron.

Note that the malleable junction, lying substantially between the upper arms and the coupling area, is relatively more narrow than the remainder of the speculum in certain preferred embodiments. In use, this allows the speculum to be manually bent downward around an axis substantially perpendicular to its longitudinal axis, the degree of bending achievable being substantially independent of the positions of the upper arms. The required degree of bending for each patient is determined by the surgeon, who shapes the speculum so that the coupling area couples substantially with the apron to form a smooth surface to guide fluid draining from the vagina. Draining fluid flows over the malleable junction and coupling area, and thence via the superior surface of the apron to the mouth of the funnel, and then into the funnel.

Besides providing a fluid drainage path that conforms to the individual patient, the speculum shaping process described above confers an additional advantage over a conventional speculum. Because that part of the speculum which in use resides outside the vagina is preferably bent downward, and that part of the speculum which in use resides inside the vagina is preferably molded to the vaginal contour, interference by the speculum with an endoscope or other instrument inserted within the vagina is minimized, while an effective guide to the funnel for fluid draining from the vagina is provided.

The measuring-collecting container of the present invention is preferably an unbreakable container of sufficient translucency to allow visual determination of fluid levels inside the container by an observer. A volume scale is preferably embossed or otherwise affixed to the container to allow rapid and accurate determination of the volume of its contents. An auxiliary connection is preferably provided on the container to accept an irrigation fluid drain line from the endoscope.

BRIEF DESCRIPTION OF THE DRAWINGS

FIG. 1A schematically illustrates a preferred embodiment of a malleable speculum of the speculum-apron-funnel-splash shield assembly.

FIG. 1B schematically illustrates a cross-section of the malleable speculum of FIG. 1A.

DETAILED DESCRIPTION

Fluid Collector Fabrication and Function

The funnel comprises a substantially frusto-conically shaped wall having an inner surface and an outer surface, and perforations within a section of the wall to admit fluid into the funnel. In preferred embodiments, fluid flowing over the splash shield is directed through perforations in the funnel wall and into the funnel. The funnel portion of the apron-funnel-splash shield assembly therefore comprises a first and a second fluid entrance. The first fluid entrance (i.e., through the mouth of the funnel) is substantially contiguous with the apron and receives fluid flowing over the apron as well as fluid which falls by gravity directly into the funnel mouth. The second fluid entrance, through the perforated portion of the funnel wall, receives fluid which falls on the splash shield and is then directed by the splash shield to flow into the funnel through the perforations. The funnel mouth is preferably held open by malleable stays to receive fluid which flows out of the vagina over the superior surface of the speculum as it is inserted in the vagina of a patient in the lithotomy position, and over the apron. In this open position, the funnel mouth can also receive fluid released from endoscopic instruments which are proximate to but not within the vagina.

The apron, splash shield, and funnel are similarly fabricated of substantially pliable, waterproof or water-resistant sheet material (e.g., sheet polyethylene or waterproof paper). Sealingly coupling the splash shield to the funnel means, e.g., attaching the splash shield to the outer funnel wall directly or indirectly in a substantially waterproof manner, as with waterproof adhesive or a welded plastic seam or a snap fit waterproof seam, at a location which would, in use, be proximate to and below the perforated portion of the funnel wall.

Illustrated Embodiments

Figure 2A:
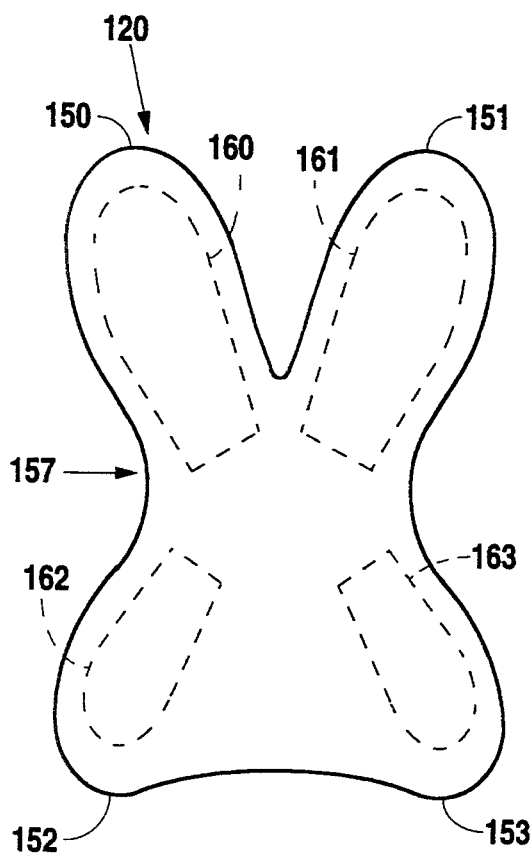
FIGS. 2A, 2B, 2C and 2D schematically illustrate alternative preferred embodiments of a malleable speculum.
Figure 2B:
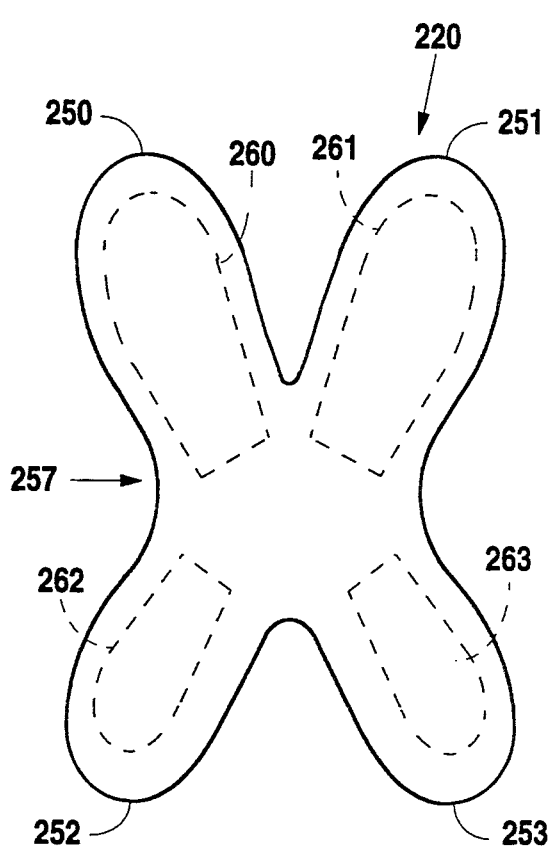
Figure 2C:
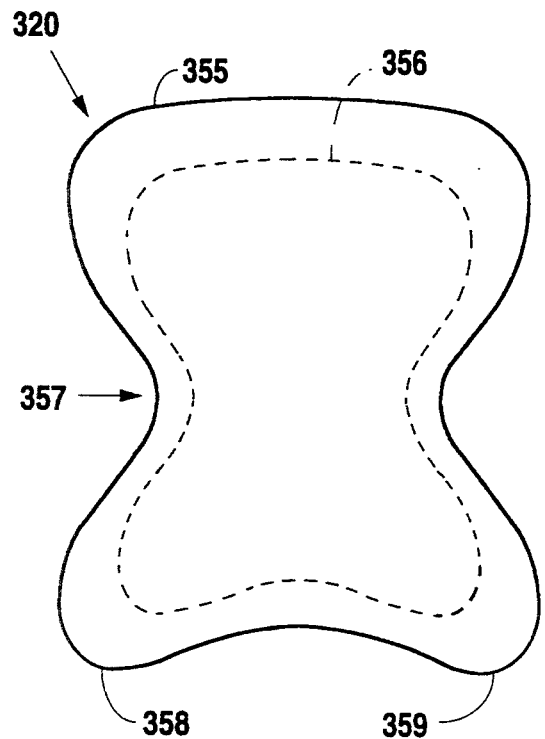
Figure 2D:
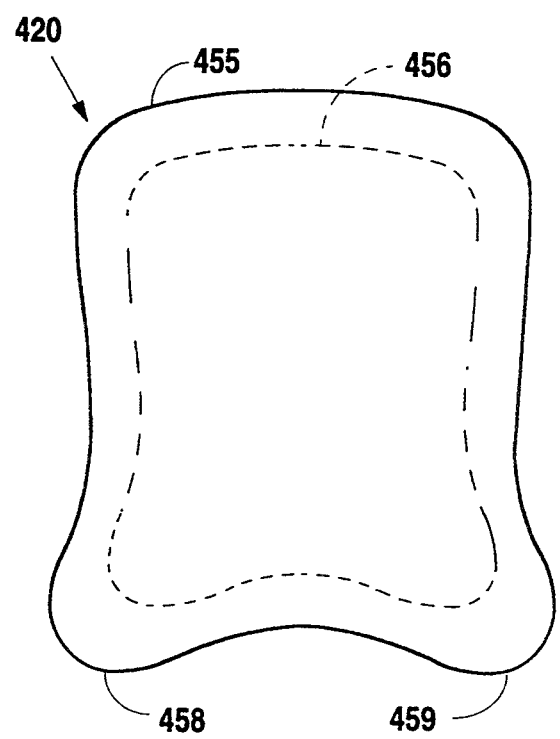
Figure 3:
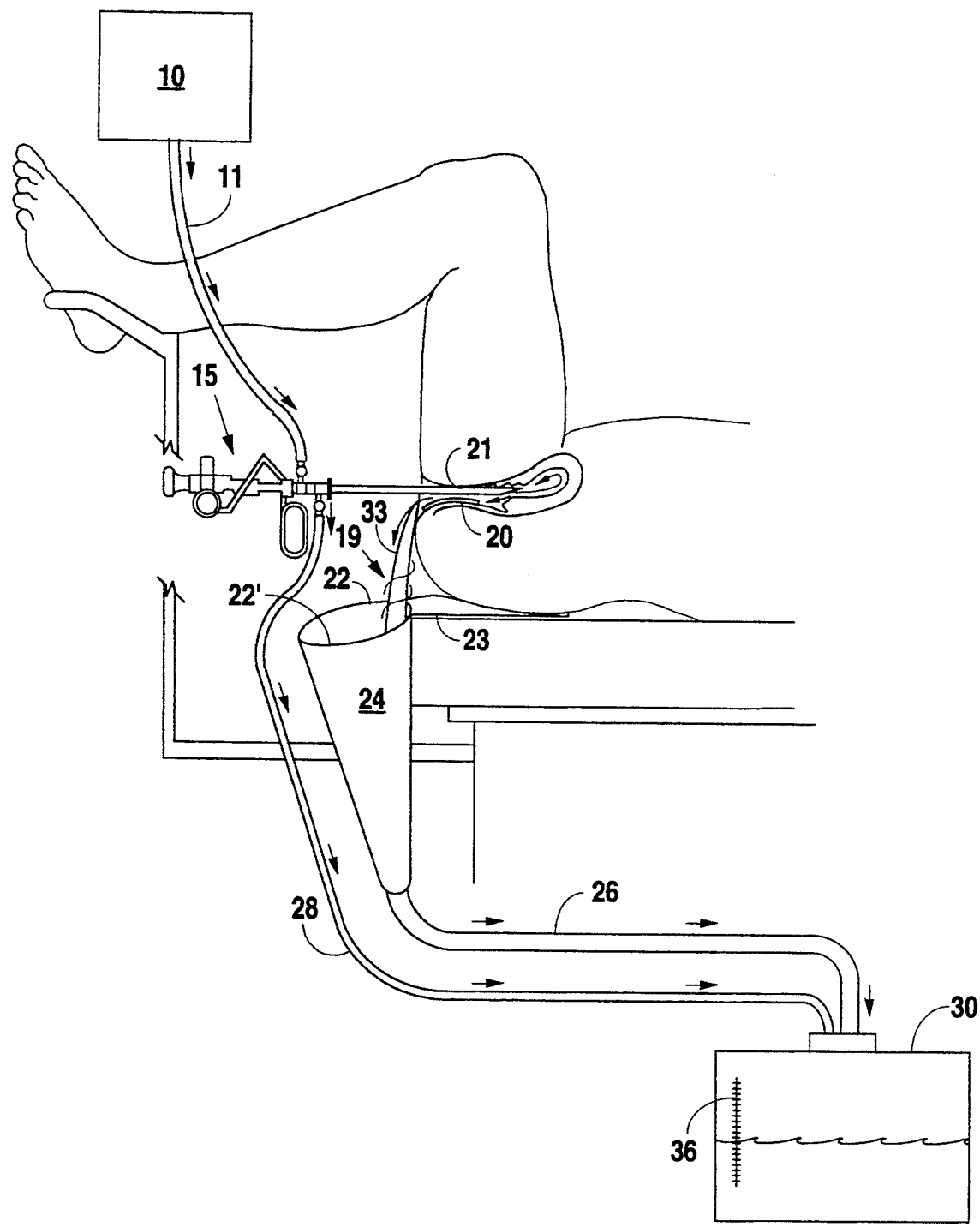
FIG. 3 schematically illustrates a side view of the speculum-apron-funnel-splash shield assembly in use on a patient undergoing endoscopy in the lithotomy position.
Figure 4:
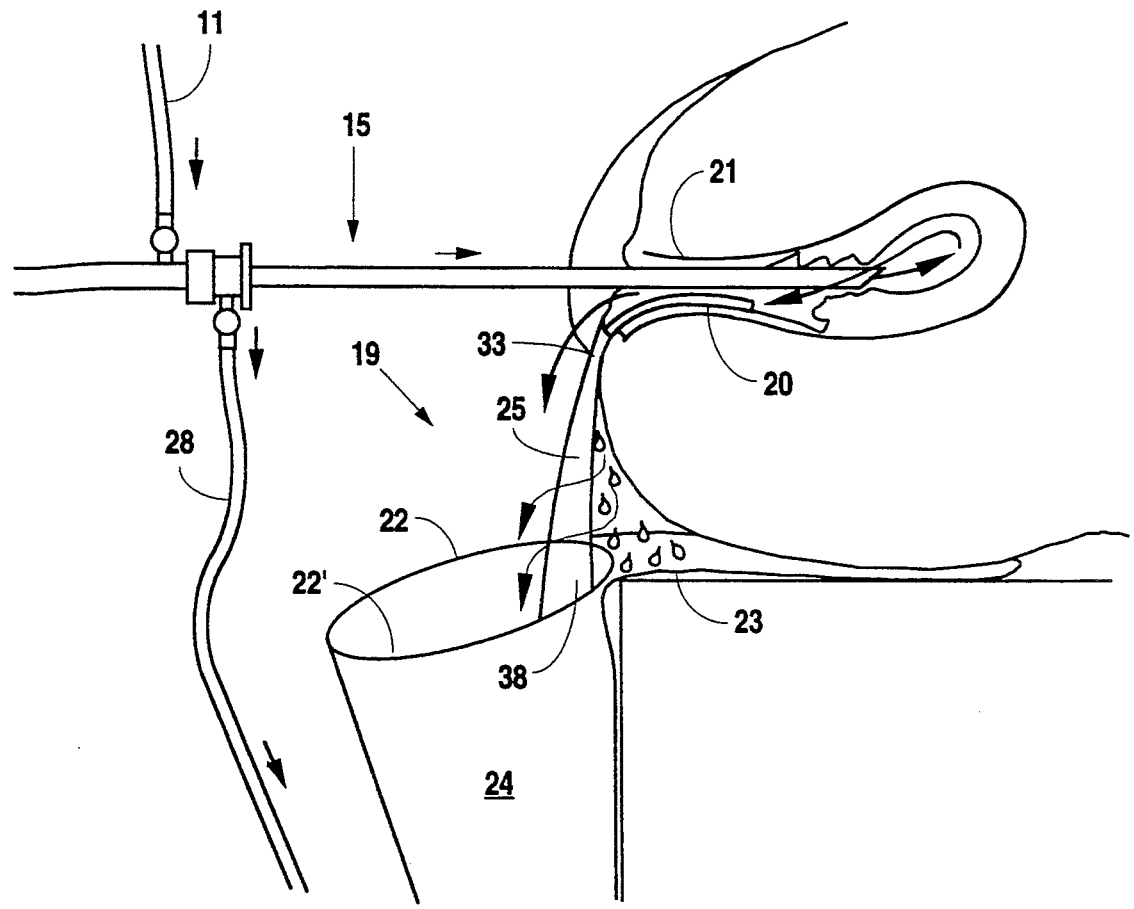
FIG. 4 schematically illustrates details of the speculum-apron-funnel-splash shield assembly in use on a patient in the lithotomy position.
Figure 6:
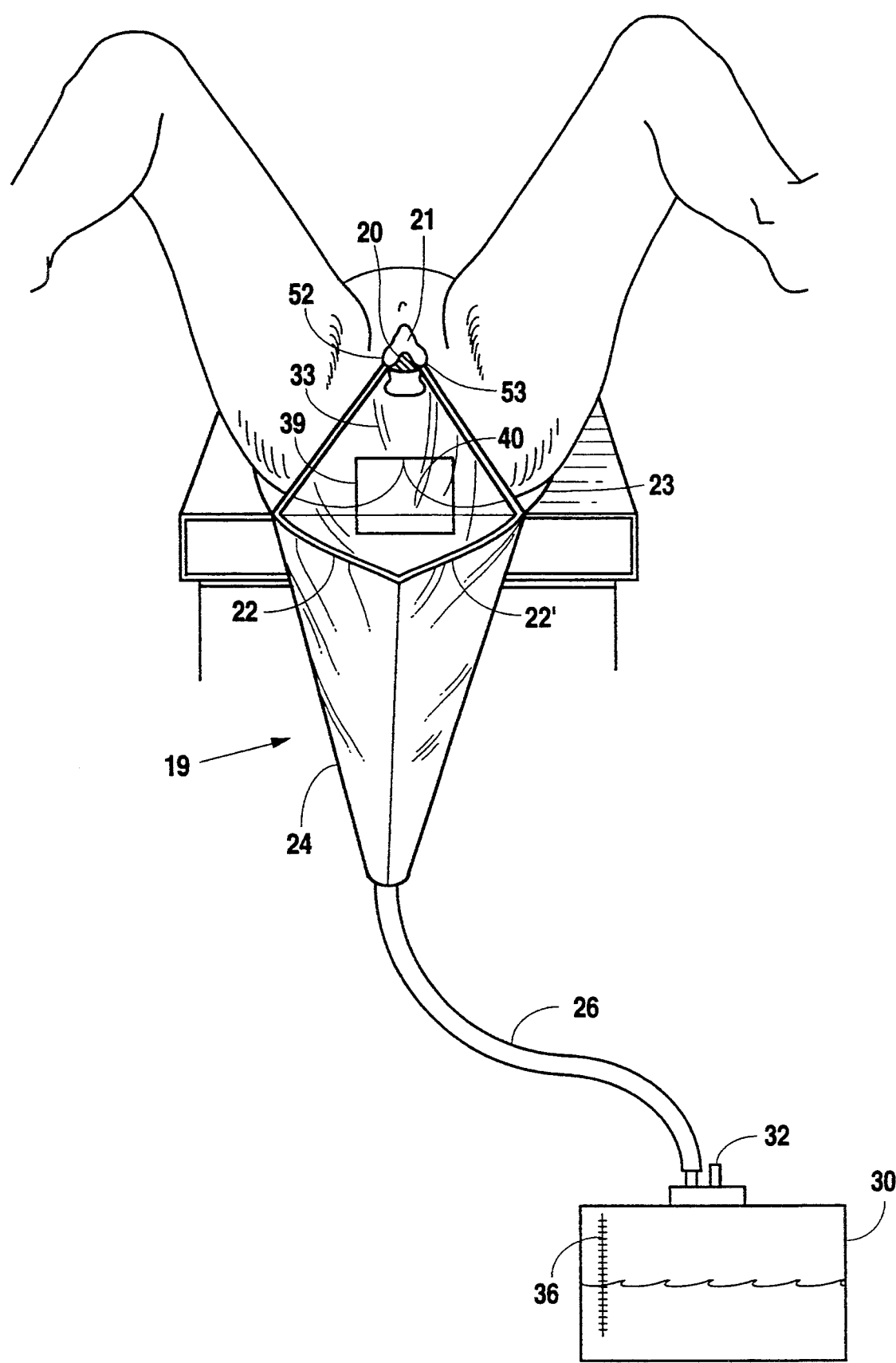
FIG. 6 schematically illustrates a frontal view of the speculum-apron-funnel-splash shield assembly in use.

FIGS. 1A and 1B illustrate a preferred embodiment of a malleable speculum 20 of speculum-apron-funnel-splash shield assembly 19 (see FIGS. 3, 4 and 6). Speculum 20 is preferably formed of pliable, biocompatible material (e.g., polyethylene or silicone rubber) in a substantially sheet-like or thin-slab (i.e., planar) form (see FIG. 1B), and having a substantially cruciate peripheral shape similar to that of the letter X (e.g., a "butterfly" or analogous shape having four arms or protuberances). Upper arms 50,51 of speculum 20 are adapted for insertion into the vagina 21 (see FIGS. 3–6) and for molding to the shape of the (dilated) vagina 21 during insertion in a manner which will reduce interference with instruments subsequently inserted within the (dilated) vagina 21.

Adaptation of upper arms 50,51 for insertion into the vagina 21 preferably includes provision of sufficient flexibility within malleable speculum 20 around an axis substantially colinear with axis A—A' to allow speculum 20 to be folded substantially along axis A—A', thus changing from a configuration wherein upper arms 50,51 are substantially coplanar to a configuration wherein upper arms 50,51 are substantially parallel.

Adaptation of upper arms 50,51 for molding to the shape of the (dilated) vagina 21 during insertion preferably includes incorporation of malleable metallic stays 65–70 and/or analogous malleable material (e.g., plastics, viscous jells or putty-like compositions) having the effect of malleable stays 65–70 within speculum 20. The stays 65–70 or analogous malleable material couple upper arms 50,51 so that arms 50,51 can be manually spread apart after vaginal insertion and molded to conform to the (dilated) vaginal wall contour, retaining the molded shape thereafter in an anesthetized patient. Thus, the molded space between arms 50,51 comprises a substantially free passage for a uterine endoscope within the (dilated) vagina 21 and also for fluid drainage from the (dilated) vagina 21. FIG. 1A includes a schematic illustration of malleable stays 65–70 or analogous malleable material coupling upper arms 50,51, lower arms 52,53, arms 50,53, arms 50,52, arms 51,52, and arms 51,53.

Note that arms 50–53 comprise reinforcement areas 60–63 respectively, reinforcement areas 60–63 acting to anchor the ends of malleable stays 65–70 which pass into the respective arms 50–53. Reinforcement areas 60–63 each comprise at least one layer of pliable sheet material or analogous physical restraint coupled to the ends of malleable stays 65–70 which pass into the respective arms 50–53, said pliable sheet or said physical restraint also being coupled to arms 50–53 respectively. Note that said pliable sheet may comprise a malleable sheet.

The region of malleable speculum 20 which lies within a space substantially bounded by upper arms 50,51 and lower arms 52,53, and which is traversed by malleable stays 65–70, comprises the malleable junction 57. The junction 57 is a relatively narrow part of speculum 20 which allows bending about an axis substantially perpendicular the longitudinal axis of speculum 20. As illustrated in FIGS. 3–6, speculum 20 is preferably bent downward to sealingly couple with apron 33, the coupling occuring at a part of speculum 20 called the coupling area, which is continuous with the malleable junction 57. In FIG. 1A, lower arms 52,53 of speculum 20 comprise the coupling area with apron 33 (illustrated in FIGS. 3–6).

FIGS. 2A, 2B, 2C and 2D illustrate preferred embodiments of a malleable speculum 120, 220,320,420 which differ in certain respects from malleable speculum 20. Speculums 120,220 are illustrated without malleable stays, comprising instead sheet malleable materials having sufficient stiffness for use in maintaining a dilated vaginal contour in use without need for stiffening with malleable stays. However, reinforcement areas 160–163, 260–263, 356 and 456 may each comprise at least one malleable sheet which may add to speculum stiffness.

Protuberances 152,153 are analogous to lower arms 52,53 (see FIG. 1A). Similarly, protuberances 252,253 are analogous to lower arms 52,53. Similarly, protuberances 358,359 are analogous to lower arms 52,53. Similarly, protuberances 458,459 are analogous to lower arms 52,53. Note that junctions 157,257,357 are analogous to malleable junction 57 (see FIG. 1A). In certain preferred embodiments (see FIG. 2D) the function of malleable junction 57 is obtained through appropriate choice of speculum materials rather than through speculum narrowing.

FIGS. 3–6 schematically illustrate speculum 20 as it is inserted into a patient's vagina 21, the patient being in the lithotomy position. Fluid flow in FIGS. 3–6 is indicated by black arrows. Lower arms 52,53 of speculum 20 are coupled through apron 33 to stays 22,22' which act to keep the mouth of funnel 24 open and to support funnel 24 which is suspended below stays 22,22'. Stays 22,22' preferably comprise malleable metallic wires or strips and/or analogous viscous jell or putty-like material coupled to funnel 24 so that in use, the mouth of funnel 24 is effectively held open to receive fluid flowing from the vagina 21 over the superior surface of speculum 20 which is inserted within the vagina 21.

Speculum-apron-funnel-splash shield 19 has a first fluid entry port at the mouth of funnel 24, the fluid entry port being held open to receive fluid by stays 22,22'. A second fluid entry port comprises a perforated portion 25 of funnel 24. Splash shield 23 is sealingly coupled to funnel 24 to allow fluid (not shown) which may fall on splash shield 23 to drain into funnel 24 through perforated portion 25. The location of the coupling of splash shield 23 to funnel 24 is such that in use, the coupling will be adjacent to and inferior to the inferior border 38 of perforated portion 25, thus allowing the drainage of substantially all fluid striking splash shield 23 through perforated portion 25 for collection through funnel 24.

Note that the perforations comprising perforated portion 25 are optionally but preferably substantially covered by a flexible waterproof or water resistant flow diverter sheet 39 which is sealingly coupled along what is, in use, a superior portion of its periphery 40. The coupling is to the funnel 24, specifically to the opposite side of this portion from that to which the splash shield 23 is sealingly coupled. In use, the flow diverter sheet 39 acts to prevent fluid which flows over the apron 33 and into the funnel 24 from flowing through the perforated portion 25, directing the flow instead into the funnel 24 for collection and measurement. The flow diverter sheet 39 also acts in use as a one-way valve (i.e., a flap valve) which allows fluid flow from the splash shield 23 through the perforated portion 25 and thence into the funnel 24 for collection and eventual measurement in container 30.

Fluid which collects in funnel 24 is directed through flexible, waterproof hose 26 to funnel connector 34 on measuring-collecting container 30. Container 30 is preferably unbreakable and sufficiently translucent or transparent to allow visual determination of any fluid level within it. Container 30 preferably has a scale 36 affixed to it for visual determination of fluid volume contained therein. Container 30 also has connector 32 for drain hose 28 which drains endoscope 15. Fluid is supplied to endoscope 15 from fluid measuring-dispensing container 10 through flexible hose 11.

Used during endoscopic surgery on a patient and in conjunction with an irrigation fluid measuring-dispensing container 10, the speculum-apron-funnel-splash shield assembly 19 and measuring-collecting container 30 of the present invention provide means to collect and measure substantially all irrigation fluid dispensed during endoscopic but not absorbed by a patient. By subtracting the measured volume of fluid collected in container 30 from the measured volume of irrigation fluid dispensed from container 10, an estimate of the amount of irrigation fluid absorbed during endoscopic surgery may be obtained. These advantages are achieved without substantial interference with the surgeon's use of the endoscope 15.

Figure 7:
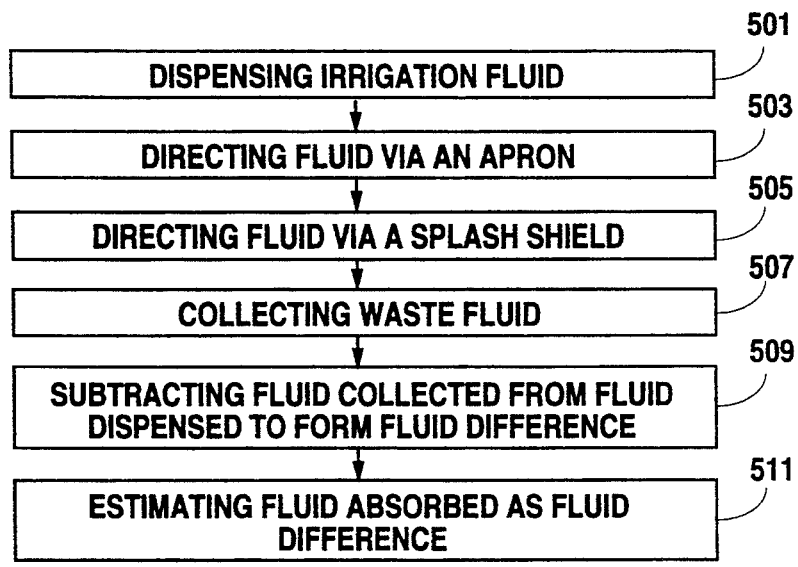
FIG. 7 illustrates in block diagram form a method of estimating an amount of fluid absorbed by a patient undergoing endoscopic surgery.
Figure 5:
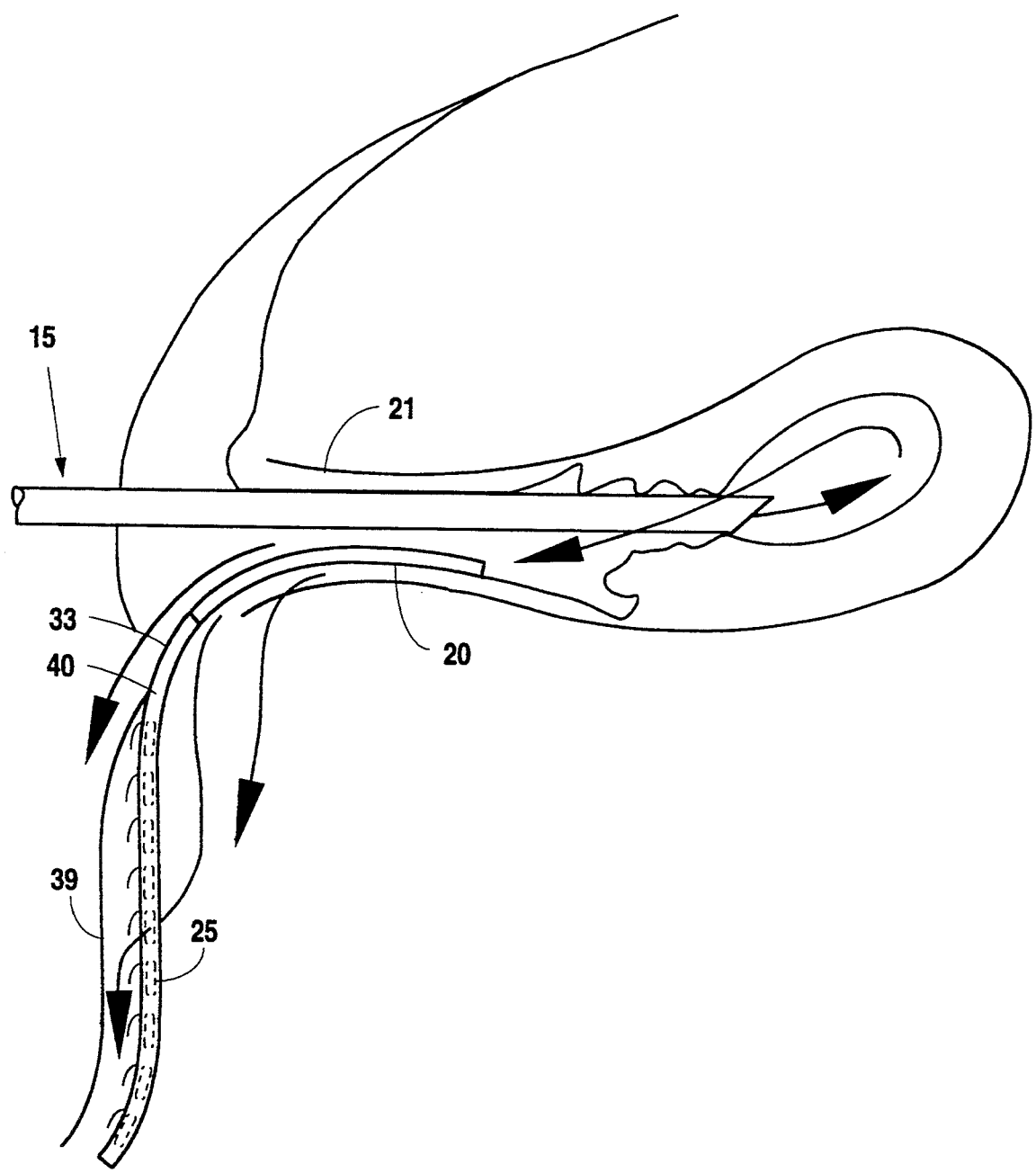
FIG. 5 schematically illustrates a flow diverter sheet and related structures and fluid flow pathways.

A method of estimating an amount of irrigation fluid absorbed by a patient undergoing endoscopic surgery is illustrated in block diagram form in FIG. 7. The method comprises dispensing a measured amount of irrigation fluid during the surgery (dispensing irrigation fluid 501); directing waste irrigation fluid into a funnel via an apron (directing fluid via an apron, 503); directing waste irrigation fluid into said funnel via a splash shield (directing fluid via a splash shield, 505); collecting a measured amount of waste irrigation fluid directed into said funnel (collecting waste fluid, 507); subtracting said measured amount of fluid collected from said measured amount of irrigation fluid dispensed during the surgery to form a fluid difference amount (subtracting fluid collected from fluid dispensed to form fluid difference, 509); and estimating said fluid difference amount as an amount of irrigation fluid absorbed by the patient undergoing endoscopic surgery (estimating fluid absorbed as fluid difference, 511).

What is claimed is:

1. A fluid collector, comprising
   a malleable speculum having a longitudinal axis and a coupling area;
   an apron having a first apron edge spaced substantially apart from a second apron edge, said first apron edge being sealingly coupled to said speculum proximate said coupling area;
   a funnel having a funnel mouth, inner and outer surfaces, and a perforated wall section, said funnel being sealingly coupled to said second apron edge proximate said funnel mouth; and
   a splash shield having a first splash shield edge spaced substantially apart from a second splash shield edge, said second splash shield edge being placeable under a patient's buttocks, and said first splash shield edge being sealingly coupled to said funnel outer surface adjacent to and inferior to said perforated wall section, thus allowing drainage of substantially all fluid striking said splash shield through said perforated wall section for collection through said funnel.

2. The fluid collector of claim 1 wherein said speculum comprises manually expandable first and second upper arms to establish sufficient vaginal patency to facilitate endoscopic surgery.

3. The fluid collector of claim 1 additionally comprising a flow diverter, said flow diverter being coupled to said funnel inner surface superior to said perforated wall section.

* * * * *

UNITED STATES PATENT AND TRADEMARK OFFICE
CERTIFICATE OF CORRECTION

PATENT NO. : 5,395,354

DATED : March 7, 1995

INVENTOR(S) : Thierry G. Vancaillie

It is certified that error appears in the above-identified patent and that said Letters Patent is hereby corrected as shown below:

Column 1, line 27, delete "surgeoffs" and replace with --surgeon's--.

Column 3, line 12, delete "Use" and replace with --use--.

Column 10, line 57, delete "i" and replace with --1--.

Signed and Sealed this

Fourth Day of July, 1995

*Attest:*

BRUCE LEHMAN

*Attesting Officer*     *Commissioner of Patents and Trademarks*